(12) United States Patent
Oh et al.

(10) Patent No.: US 7,307,139 B2
(45) Date of Patent: Dec. 11, 2007

(54) DIAMINE COMPOUND HAVING DENDRON SIDE CHAIN AND LIQUID CRYSTAL ALIGNMENT MATERIAL PRODUCED USING THE SAME

(75) Inventors: Jae Min Oh, Suwon-Shi (KR); Bum Jin Lee, Seongnam-Shi (KR); Yusuke Tsuda, Kurume (JP)

(73) Assignee: Cheil Industries Inc., Kumi-shi (KR)

( * ) Notice: Subject to any disclaimer, the term of this patent is extended or adjusted under 35 U.S.C. 154(b) by 196 days.

(21) Appl. No.: 10/536,854

(22) PCT Filed: Oct. 8, 2004

(86) PCT No.: PCT/KR2004/002578

§ 371 (c)(1),
(2), (4) Date: May 27, 2005

(87) PCT Pub. No.: WO2005/033248

PCT Pub. Date: Apr. 14, 2005

(65) Prior Publication Data

US 2006/0073350 A1    Apr. 6, 2006

(30) Foreign Application Priority Data

Oct. 9, 2003    (KR) ...................... 10-2003-0070378

(51) Int. Cl.
*C08G 69/08* (2006.01)
(52) U.S. Cl. .................................................... 528/310
(58) Field of Classification Search ................ 528/310
See application file for complete search history.

(56) References Cited

U.S. PATENT DOCUMENTS 5,420,233 A      5/1995  Isogai et al.
6,746,730 B1 *   6/2004  Tanioka et al. .............. 428/1.1

FOREIGN PATENT DOCUMENTS

| JP | 11-84391 | 7/1989 |
|----|----------|--------|
| JP | 6-136122 | 5/1994 |
| JP | 9-230353 | 9/1997 |
| JP | 9-272740 | 10/1997 |
| JP | 11-193347 | 7/1999 |
| JP | 2000-305085 | 11/2000 |
| WO | WO02/062873 | * 8/2002 |

* cited by examiner

*Primary Examiner*—James J. Seidleck
*Assistant Examiner*—Gregory Listvoyb
(74) *Attorney, Agent, or Firm*—Hamre, Schumann, Mueller & Larson, P.C.

(57) ABSTRACT

Disclosed herein are a novel diamine compound having a dendron side chain and a liquid crystal alignment material produced using the diamine compound. Specifically, the diamine compound is used to prepare a polyamic acid, which is then used to produce the liquid crystal alignment material. According to the liquid crystal alignment material, the pretilt angle of a liquid crystal is easy to control, and the alignment properties of a liquid crystal are good. Particularly, since the liquid crystal alignment material shows superior chemical resistance to washing solvents used in LCD panel fabrication processes, it has an advantage in that the alignment properties of a liquid crystal are not degraded even after washing.

10 Claims, 1 Drawing Sheet

DIAMINE COMPOUND HAVING DENDRON SIDE CHAIN AND LIQUID CRYSTAL ALIGNMENT MATERIAL PRODUCED USING THE SAME

TECHNICAL FIELD

The present invention relates to a diamine compound having a dendron side chain, and a liquid crystal (LC) alignment material produced using the diamine compound. More particularly, the present invention relates to a technique for providing an LC alignment material by introducing a dendron side chain into a diamine compound wherein the pretilt angle of a liquid crystal is easy to control, the alignment properties of a liquid crystal are good, and the chemical resistance of the alignment material during washing is superior.

BACKGROUND ART

In general, conventional polyimide resins for liquid crystal alignment films are prepared from the polycondensation of an aromatic dianhydride, e.g., pyromellitic dianhydride (PMDA) or biphthalic dianhydride (BPDA), and an aromatic diamine, e.g, para-phenylenediamine (p-PDA), meta-phenylenediamine (m-PDA), 4,4-methylenedianiline (MDA), 2,2-bisaminophenylhexafluoropropane (HFDA), meta-bisaminophenoxydiphenylsulfone (m-BAPS), para-bisaminophenoxydiphenylsulfone (p-BAPS), 4,4-bisaminophenoxyphenylpropane (BAPP) or 4,4-bisaminophenoxyphenylhexafluoropropane (HF-BAPP), as monomers.

DISCLOSURE

Technical Problem

Polyimide liquid crystal alignment films produced from the aromatic dianhydrides and the diamines are superior in thermal stability, chemical resistance, mechanical properties, and the like. However, the polyimide liquid crystal alignment films have problems of poor transparency and solubility due to the formation of a charge transfer complex, and poor electrooptical properties. In efforts to solve these problems, Japanese Patent Laid-open No. Hei 11-84391 describes the introduction of an alicyclic dianhydride monomer or an alicyclic diamine, and Japanese Patent Laid-open No. Hei 06-136122 discloses the introduction of a functional diamine having a side chain or a functional dianhydride having a side chain in order to increase the pretilt angle of a liquid crystal and improve the stability of a liquid crystal. Further, a vertical alignment type alignment film was developed that enables liquid crystal molecules to be aligned vertically to the surface of the film to constitute an LCD panel in a vertical alignment (VA) mode (see, U.S. Pat. No. 5,420,233).

As the market for liquid crystal display devices has recently expanded, there is a continuing demand for high-quality display devices. Further, as technologies for large-area liquid crystal display devices have made remarkable progress, there exists a strong need to produce an alignment film with high productivity. Thus, there is a continuing need in the art to develop a high-performance liquid crystal alignment film capable of sufficiently meeting different characteristics, e.g., few defects in LCD fabrication processes, excellent electrooptical properties, and high reliability, required in various liquid crystal display devices.

[Technical Solution]

The present inventors have earnestly and intensively conducted research to solve the above-mentioned problems of the prior art. As a result, the present inventors have found that a liquid crystal alignment material produced using a functional diamine with a dendron side chain enables easy control of pretilt angle and uniform alignment of a liquid crystal, and shows superior chemical resistance during washing, thus accomplishing the present invention.

Specifically, in accordance with one aspect of the present invention, there is provided a diamine compound represented by Formula 1 below:

Formula 1 wherein

A is a single bond, —O—, —COO—, —CONH—, or —OCO—;

B is a single bond, —O—, —COO—, —CONH—, or —OCO—;

the substituents C are independently a single bond, —O—, —COO—, —CONH—, or —OCO—; and the substituents D are independently a $C_{1-20}$ linear, branched or cyclic alkyl group which may be substituted with at least one halogen atom, or a functional group represented by Formula 2 below:

Formula 2 wherein the substituents C' are independently —O—, —COO—, —CONH—, or —OCO—; and the substituents D' are independently a $C_{1-20}$ linear, branched or cyclic alkyl group, or a functional group represented by Formula 3 below:

Formula 3 wherein the substituents C" are independently —O—, —COO—, —CONH—, or —OCO—; and the substituents D" are independently a $C_{1-20}$ linear, branched or cyclic alkyl group, or a functional group represented by Formula 4 below:

Formula 4 wherein the substituents C''' are independently —O—, —COO—, —CONH—, or —OCO—; and the substituents D''' are independently a $C_{1-20}$ linear, branched or cyclic alkyl group.

In accordance with another aspect of the present invention, there is provided a polyamic acid prepared by copolymerizing the diamine compound, an alicyclic dianhydride, an aromatic cyclic dianhydride, and optionally, an aromatic cyclic diamine and/or a siloxane-based diamine.

In accordance with another aspect of the present invention, there is provided a soluble polyimide prepared by wholly or partially imidizing the polyamic acid.

In accordance with another aspect of the present invention, there is provided a mixture of the polyamic acid and the soluble polyimide.

In accordance with another aspect of the present invention, there is provided a liquid crystal alignment film produced by dissolving the polyamic acid, the soluble polyimide, or the mixture thereof in a solvent, coating the solution on a substrate, and wholly or partially imidizing the coated solution.

In accordance with yet another aspect of the present invention, there is provided a liquid crystal display device comprising the liquid crystal alignment film.

Hereinafter, the present invention will be explained in detail.

The present invention provides a functional diamine represented by Formula 1 below:

(1)

wherein

A is a single bond, —O—, —COO—, —CONH—, or —OCO—;

B is a single bond, —O—, —COO—, —CONH—, or —OCO—;

the substituents C are independently a single bond, —O—, —COO—, —CONH—, or —OCO—; and the substituents D are independently a $C_{1-20}$ linear, branched or cyclic alkyl group which may be substituted with at least one halogen atom, or a functional group represented by Formula 2 below:

(2)

wherein the substituents C' are independently —O—, —COO—, —CONH—, or —OCO—; and the substituents D' are independently a $C_{1-20}$ linear, branched or cyclic alkyl group, or a functional group represented by Formula 3 below:

(3)

wherein the substituents C″ are independently —O—, —COO—, —CONH—, or —OCO—; and the substituents D″ are independently a $C_{1-20}$ linear, branched or cyclic alkyl group, or a functional group represented by Formula 4 below:

(4)

wherein the substituents C‴ are independently —O—, —COO—, —CONH—, or —OCO—; and the substituents D‴ are independently a $C_{1-20}$ linear, branched or cyclic alkyl group.

Specific examples of the functional diamine compound include compounds represented by Formulae 5 and 6 below:

Formula 5

Formula 6

However, the compounds of Formulae 5 and 6 are provided for illustrative purposes only, and the structure of the functional diamine according to the present invention is not limited thereto.

Since the functional diamine monomer of the present invention has a benzene ring skeleton, acting as a spacer, in its side chain, less steric hindrance is caused. Accordingly, this structural effect minimizes a decrease in the reactivity of the diamine monomer, assists in the alignment of liquid crystal molecules in the direction of the side chain, and improves the chemical resistance of an alignment film to be produced, thus greatly contributing to an improvement in the resistance to washing. In addition, since a plurality of alkyl groups can be simultaneously introduced into the side chain to form a dendron structure, even a low content of the diamine monomer results in an increased pretilt angle. These characteristics of the functional diamine monomer stabilize the pretilt angle of a liquid crystal, and align liquid crystal molecules in a direction perpendicular to the surface of a alignment film to be produced.

The present invention provides a polyamic acid prepared by copolymerizing the functional diamine having a dendron side chain, an alicyclic dianhydride, an aromatic cyclic dianhydride, and optionally, an aromatic cyclic diamine and/or a siloxane-based diamine.

The polyamic acid can be prepared from the acid dianhydride and the diamine compound by conventional copolymerization processes. These copolymerization processes are not particularly limited so long as they can be used to prepare polyamic acids. Since the polyamic acid contains the functional diamine unit, the pretilt angle of a liquid crystal is easy to control and the alignment of a liquid crystal becomes uniform. Since the pretilt angle is varied according to the content of the functional diamine monomer, the polyamic acid can be prepared by using the functional diamine alone without the use of the aromatic cyclic diamine or the siloxane-based diamine, depending on the mode of liquid crystal displays. Thereafter, the polyamic acid thus prepared can be used to produce a liquid crystal alignment film. That is, the aromatic diamine or the siloxane-based diamine is an optional component. Accordingly, the content of the functional diamine of Formula 1 in the polyamic acid is in the range of 0.1~100 mole %, preferably 0.5 mole % to 30 mole %, and more preferably 1 mole % to 20 mole %, relative to the total amount of the diamine monomers.

Examples of suitable aromatic cyclic diamines used for the preparation of the polyamic acid include, but are not limited to, para-phenylenediamine (p-PDA), 4,4-methylenedianiline (MDA), 4,4-oxydianiline (ODA), meta-bisaminophenoxydiphenylsulfone (m-BAPS), para-bisaminophenoxydiphenylsulfone (p-BAPS), 2,2-bisaminophenoxyphenylpropane (BAPP), and 2,2-bisaminophenoxyphenylhexafluoropropane (HF-BAPP).

The siloxane-based diamine used for the preparation of the polyamic acid according to the present invention has a structure represented by Formula 7 below:

Formula 7 wherein n is an integer of from 1 to 10.

The amount of the aromatic cyclic diamine and/or the siloxane-based diamine used is in the range of 0~99.9 mole %, preferably 70~99.5 mole %, and more preferably 80~99 mole %, based on the total amount of the diamine monomers.

The aromatic cyclic dianhydride used for the preparation of the polyamic acid according to the present invention causes an alignment film having a thickness of about 0.1 µm to be resistant to a rubbing process, which is carried out in order to align liquid crystal molecules in one direction, to be heat resistant to high temperature processing processes at 200° C. or above, and to be resistant to chemicals.

Examples of such aromatic cyclic dianhydrides include, but are not limited to, pyromellitic dianhydride (PMDA), biphthalic dianhydride (BPDA), oxydiphthalic dianhydride (ODPA), benzophenonetetracarboxylic dianhydride (BTDA), and hexafluoroisopropylidene diphthalic dianhydride (6-FDA).

The content of the aromatic cyclic dianhydride is between 10 mole % and 95 mole %, and preferably between 50 mole % and 90 mole %, relative to the total amount of the dianhydride monomers. If the aromatic cyclic dianhydride is used in an amount of less than 10 mole %, an alignment film to be produced is poor in mechanical properties and heat resistance. On the other hand, if the aromatic cyclic dianhydride is used in an amount exceeding 80 mole %, the electrical properties, e.g., voltage holding rate, are worsened.

The alicyclic dianhydride used for the preparation of the polyamic acid according to the present invention solves problems, for example, insolubility in common organic solvents, low transmittance in the visible light region due to the formation of a charge transfer complex, poor electrooptical properties due to high polarity, resulting from the molecular structure of the polyamic acid, etc.

Examples of the alicyclic dianhydride include, but are not limited to, 5-(2,5-dioxotetrahydrofuryl)-3-methylcyclohexene-1,2-dicarboxylic dianhydride (DOCDA), bicyclooctene-2,3,5,6-tetracarboxylic dianhydride (BODA), 1,2,3,4-cyclobutanetetracarboxylic dianhydride (CBDA), 1,2,3,4-cyclopentanetetracarboxylic dianhydride (CPDA), and 1,2,4,5-cyclohexanetetracarboxylic dianhydride (CHDA).

The content of the alicyclic dianhydride is between 5 mole % and 90 mole %, and preferably between 10 and 50 mole %, based on the total amount of the dianhydride monomers.

The polyamic acid of the present invention is highly soluble in general aprotic polar solvents, e.g., N-methyl-2-pyrrolidone (NMP), γ-butyrolactone (GBL), dimethylformamide (DMF), dimethylacetamide (DMAc), and tetrahydrofuran (THF). It is believed that the superior solubility of the polyamic acid is largely attributed to the introduction of the alicyclic dianhydride and the steric effects of the functional diamine present in a three-dimensional structure due to large steric repulsion between the three benzene rings in view of the molecular structure of the functional diamine. As liquid crystal display devices have recently become large-scale, high resolution and high quality, the printability of alignment materials has been gaining importance. Under these circumstances, good solubility has a positive influence on the printability on a substrate when the functional diamine is used to produce liquid crystal alignment films.

The polyamic acid of the present invention preferably has a number-average molecular weight of 10,000 to 500,000 g/mol. When the polyamic acid is imidized, it has a glass transition temperature of 200° C. to 350° C. depending on the imidization rate or the structure of the polyamic acid.

The present invention provides a liquid crystal alignment film produced by dissolving the polyamic acid in a solvent, coating the solution on a substrate, and wholly or partially imidizing the coated solution.

Alternatively, the liquid crystal alignment film of the present invention can be produced from a soluble polyimide alone, which is prepared by wholly or partially imidizing the polyamic acid, or a mixture of the polyamic acid and the soluble polyimide.

The alignment film shows a transmittance of 90% or higher in the visible light region, uniform alignment of a liquid crystal, and easy control of the pretilt angle of a liquid crystal within the range of 1°~90°. In addition, since the alignment film contains the functional diamine, it shows improved electrooptical properties, e.g., low refractive index and low dielectric constant.

DESCRIPTION OF THE PREFERRED EMBODIMENTS

The present invention will now be described in more detail with reference to the following examples. However, these examples are given for the purpose of illustration and are not to be construed as limiting the scope of the invention.

PREPARATIVE EXAMPLE 1

(1) Preparation of 3,4,5-tris(n-dodecyloxy)benzoyl chloride

-continued

(4)
12G1-AG

(5)
3,4,5-tris(n-dodecyloxy)benzoyl chloride

One mole of (1) was dissolved in DMF in a round-bottom flask equipped with a condenser, and then 3.9 moles of potassium carbonate was added thereto. The resulting mixture was sufficiently stirred. After 3.1 moles of (2) was added to the stirred mixture, the reaction temperature of the flask was slowly raised to 70° C. Thereafter, the reaction mixture was allowed to react for 24 hours while maintaining the temperature at 80° C. After the reaction was completed, the temperature was dropped to room temperature. The reacted solution was poured into pure water to form a precipitate. The precipitate was filtered, and washed several times to obtain a clean product (3). The product (3) was dissolved in ethanol, and then potassium hydroxide was added thereto. The ethanolic solution was refluxed for 4 hours to obtain an acid derivative (4). The acid derivative (4) was subjected to acylation by refluxing it for 4 hours together with thionyl chloride, to give 3,4,4-trisdodecyloxybenzoyl chloride (5).

(2) Preparation of 12G1-AG-terphenyldiamine

-continued (11)
12G1-AG-Terphenyldiamine

One mole of dibromobenzoic acid (6) was charged in a sufficiently dried round-bottom flask, and then THF was added thereto to dissolve the acid (6). After DCC and DMAP were added to the solution, the temperature of the flask was cooled to 0° C. While 1.1 moles of aminophenol was slowly added to the cooled solution, the reaction mixture was reacted for 30 minutes to form an intermediate (8). The intermediate (8) was dissolved in THF, and TEA as a catalyst was added thereto. To the solution was added the compound (5). The resulting mixture was reacted at room temperature for 3 hours to obtain an intermediate (9). Next, moisture and oxygen present inside a sufficiently washed and dried round-bottom flask were removed in vacuo, and instead, the flask was filled with argon (Ar) as an inert gas. The intermediate (9) was charged into the flask, and then DME was added thereto to dissolve the intermediate (9). Palladium phosphate and sodium carbonate as catalysts were added to the solution, and then 2.2 mole equivalents of aminoboronic acid (10) was added thereto. After the resulting mixture was homogeneously dissolved, the temperature of the flask was raised to 80° C. The solution was allowed to react for 24 hours while maintaining the temperature at 80° C. After completion of the reaction, the reaction solution was purified by column chromatography and recrystallization to give the final product 12G1-AG-terphenyldiamine.

Figure 1:
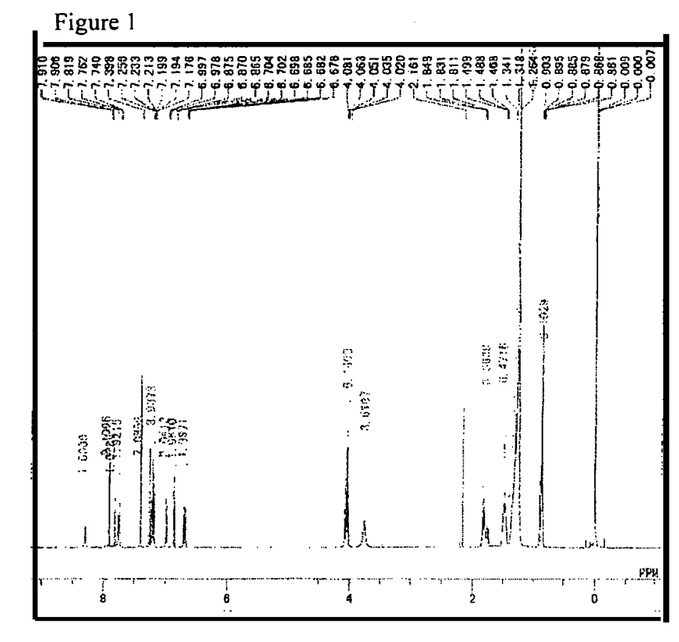
FIG. 1 is a $^1$H-NMR spectrum of a diamine compound prepared in Preparative Example 1 of the present invention.
Figure 2:
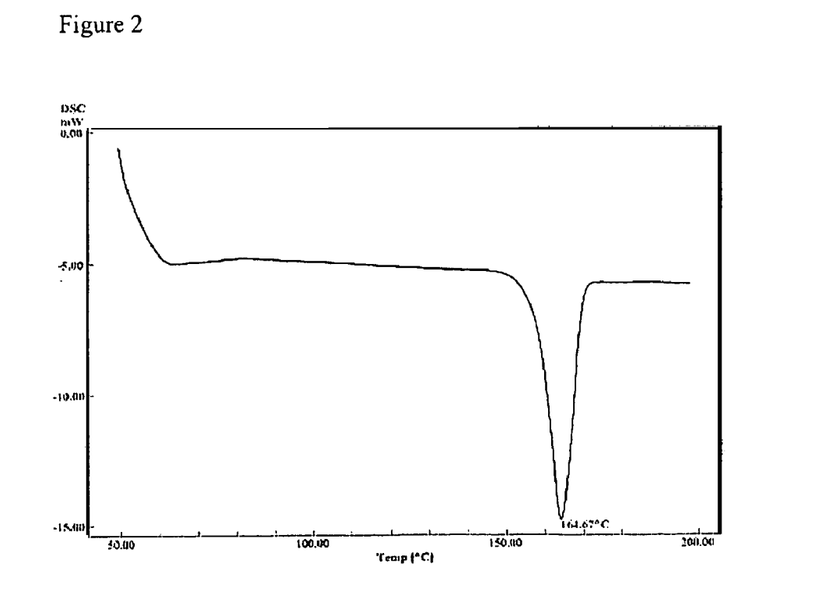
FIG. 2 is a differential scanning calorimetry (DSC) thermogram of a diamine compound prepared in Preparative Example 1 of the present invention.

The structure of the final product was identified through $^1$H-NMR spectrum, and thermal characteristics were evaluated using differential scanning calorimetry (DSC). The results are shown in FIGS. 1 and 2, respectively.

EXAMPLE 1

0.99 moles of 4,4-methylenedianiline and 0.01 moles of 12G1-AG-terphenyldiamine (dendron diamine, Formula 5) were charged into a four-neck flask equipped with a stirrer, a thermostat, a nitrogen injection apparatus and a condenser while passing nitrogen through the flask, and then N-methyl-2-pyrrolidone (NMP) was added thereto. The resulting mixture was dissolved. To the solution was added 0.5 moles of 5-(2,5-dioxotetrahydrofuryl)-3-methylcyclohexane-1,2-dicarboxylic anhydride (DOCDA) in a solid state, and 0.5 moles of pyromellitic dianhydride (PMDA). The resulting mixture was vigorously stirred. At this time, the solid content was 15% by weight. While maintaining at a temperature lower than 25° C., the reaction mixture was allowed to react for 24 hours to prepare a polyamic acid solution.

To evaluate the chemical resistance of the alignment films, the polyamic acid solution was spin coated on ITO glass substrates (10 cm×10 cm) to a thickness of 0.1 μm, cured at 70° C. and 210° C., and rubbed to produce alignment films. Thereafter, the surface of the alignment films was sufficiently washed with isopropyl alcohol and pure water, and then the alignment films were assembled to fabricate an LCD test cell. While the LCD test cell was driven by applying a voltage of 1~2V thereto, the formation of stains on the LCD test cell was observed. The results are shown in Table 1.

Further, to evaluate the alignment properties and measure the pretilt angle of a liquid crystal by rubbing, the polyamic acid solution was applied to two ITO glass substrates to a thickness of 0.1 μm, and cured at 210° C. to produce two alignment films. At this time, the spreadability and curling properties at the ends of the alignment film were observed visually or using an optical microscope to evaluate the printability of the alignment film. On the other hand, the surface of the alignment films were rubbed using a rubbing machine, the alignment films were arranged parallel to each other in such a manner that the rubbing direction of one alignment film was opposed to that of the other alignment film, and the two alignment films were sealed to fabricate a liquid crystal cell having a cell gap of 50 μm. After the liquid crystal cell was filled with liquid crystal molecules, the alignment properties of the liquid crystal were observed under an orthogonally polarized optical microscope, and the pretilt angle of the liquid crystal was measured by a crystal rotation method. The results are shown in Table 1.

EXAMPLE 2

A polyamic acid was prepared in the same manner as in Example 1, except that 0.98 moles of 4,4-methylenedianiline and 0.02 moles of 12G1-AG-terphenyldiamine were used. In accordance with the procedures described in Example 1, the alignment properties of the liquid crystal were evaluated, the pretilt angle of the liquid crystal was measured, and the chemical resistance of the alignment film was evaluated. The results are shown in Table 1.

EXAMPLE 3

A polyamic acid was prepared in the same manner as in Example 1, except that 0.95 moles of 4,4-methylenedianiline and 0.05 moles of 12G1-AG-terphenyldiamine were used. In accordance with the procedures described in Example 1, the alignment properties of the liquid crystal were evaluated, the pretilt angle of the liquid crystal was measured, and the chemical resistance of the alignment film was evaluated. The results are shown in Table 1.

EXAMPLE 4

A polyamic acid was prepared in the same manner as in Example 1, except that 0.92 moles of 4,4-methylenedianiline and 0.08 moles of 12G1-AG-terphenyldiamine were used. In accordance with the procedures described in Example 1, the alignment properties of the liquid crystal were evaluated, the pretilt angle of the liquid crystal was measured, and the chemical resistance of the alignment film was evaluated. The results are shown in Table 1.

EXAMPLE 5

A polyamic acid was prepared in the same manner as in Example 1, except that 0.85 moles of 4,4-methylenedianiline- and 0.15 moles of 12G1-AG-terphenyldiamine were used. In accordance with the procedures described in Example 1, the alignment properties of the liquid crystal were evaluated, the pretilt angle of the liquid crystal was measured, and the chemical resistance of the alignment film was evaluated. The results are shown in Table 1.

COMPARATIVE EXAMPLE 1

A polyamic acid was prepared in the same manner as in Example 1, except that 0.9 moles of 4,4-methylenedianiline and 0.1 moles of 2,4-diaminophenoxyhexadecane were used. In accordance with the procedures described in Example 1, the alignment properties of the liquid crystal were evaluated, the pretilt angle of the liquid crystal was measured, and the chemical resistance of the alignment film was evaluated. The results are shown in Table 1.

COMPARATIVE EXAMPLE 2

A polyamic acid was prepared in the same manner as in Example 1, except that 0.85 moles of 4,4-methylenedianiline and 0.15 moles of 2,4-diaminophenoxyhexadecane were used. In accordance with the procedures described in Example 1, the alignment properties of the liquid crystal were evaluated, the pretilt angle of the liquid crystal was measured, and the chemical resistance of the alignment film was evaluated. The results are shown in Table 1.

TABLE 1

| Example No. | Pretilt angle (°) | Printability | Vertical alignment | Chemical resistance |
| --- | --- | --- | --- | --- |
| Example 1 | 3.6 | Good | No | Good |
| Example 2 | 7.1 | Good | No | Good |
| Example 3 | 79.0 | Good | Weak | Good |
| Example 4 | =89 | Good | Good | Good |
| Example 5 | =89 | Good | Good | Good |
| Comparative Example 1 | 6.7 | Good | No | Poor |
| Comparative Example 2 | 12.7 | Weak | No | Poor |

[Advantageous Effects]

As apparent from the above description, the present invention provides a liquid crystal alignment material wherein the alignment properties of a liquid crystal are good, the pretilt angle of a liquid crystal is easy to control, and the chemical resistance of the alignment material during washing is superior.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

DESCRIPTION OF DRAWINGS

The above and other objects, features and other advantages of the present invention will be more clearly understood from the following detailed description taken in conjunction with the accompanying drawings, in which.

The invention claimed is:

1. A diamine compound represented by Formula 1 below:

(1)

wherein

A is a single bond, —O—, —COO—, —CONH—, or —OCO—;

B is a single bond, —O—, —COO—, —CONH—, or —OCO—;

the substituents C are independently a single bond, —O—, —COO—, —CONH—, or —OCO—; and the substituents D are independently a $C_{1-20}$ linear, branched or cyclic alkyl group which may be substituted with at least one halogen atom, or a functional group represented by Formula 2 below:

(2)

wherein the substituents C' are independently —O—, —COO—, —CONH—, or —OCO—; and the substituents D' are independently a $C_{1-20}$ linear, branched or cyclic alkyl group, or a functional group represented by Formula 3 below:

(3)

wherein the substituents C" are independently —O—, —COO—, —CONH—, or —OCO—; and the substituents D" are independently a $C_{1-20}$ liner, branched or cyclic alkyl group, or a functional group represented by Formula 4 below:

(4)

wherein the substituents C'" are independently —O—, —COO—, —CONH—, or —OCO—; and the substituents D'" are independently a $C_{1-20}$ linear, branched or cyclic alkyl group.

2. The diamine compound according to claim 1, wherein the diamine compound is a compound represented by Formula 5 or 6 below:

(5)

-continued (6)

3. A polyamic acid prepared by copolymerizing the diamine compound according to claim 1, an alicyclic dianhydride, an aromatic cyclic dianhydride, and optionally, an aromatic cyclic diamine and/or a siloxane-based diamine.

4. The polyamic acid according to claim 3, wherein the diamine compound according to claim 1 is present in an amount of 0.1~100 mole %, and the aromatic cyclic diamine and the siloxane-based diamine are present in an amount of 0~99.9 mole %, based on the total amount of the diamine monomers.

5. The polyamic acid according to claim 3, wherein the aromatic cyclic dianhydride is present in an amount of 10~95 mole %, and the alicyclic dianhydride is present in an amount of 5~90 mole %, based on the total amount of the dianhydride monomers.

6. The polyamic acid according to claim 3, wherein the polyamic acid has a number-average molecular weight of 10,000 to 500,000 g/mol.

7. A soluble polyimide prepared by wholly or partially imidizing the polyamic acid according to claim 3.

8. A mixture of the polyamic acid according to claim 3 and the soluble polyimide according to claim 7.

9. A liquid crystal alignment film produced by dissolving the polyamic acid according to claim 3, the soluble polyimide according to claim 7 or the mixture according to claim 8 in a solvent, coating the solution on a substrate, end wholly or partially imidizing the coated solution.

10. A liquid crystal display device comprising the liquid crystal alignment film according to claim 9.

* * * * *